United States Patent [19]
Voigt et al.

[11] Patent Number: 4,568,707
[45] Date of Patent: Feb. 4, 1986

[54] SILICONE PASTES FORMULATED WITH A STRUCTURAL VISCOSITY FOR IMPRESSION MATERIALS

[75] Inventors: Reiner Voigt; Peter Schwabe, both of Leverkusen, Fed. Rep. of Germany

[73] Assignee: Bayer Aktiengesellschaft, Leverkusen, Fed. Rep. of Germany

[21] Appl. No.: 710,820

[22] Filed: Mar. 12, 1985

[30] Foreign Application Priority Data

Mar. 16, 1984 [DE] Fed. Rep. of Germany ....... 3409720

[51] Int. Cl.$^4$ ............................. C08K 5/10; A61C 9/00
[52] U.S. Cl. ..................................... 523/109; 524/773; 524/862; 433/214
[58] Field of Search ................ 523/109; 524/310, 773, 524/862; 433/214

[56] References Cited

U.S. PATENT DOCUMENTS

| 4,035,453 | 7/1977 | Hittmair et al. | 523/109 |
| 4,222,983 | 9/1980 | August et al. | 524/862 |
| 4,513,115 | 4/1985 | Beers | 524/773 |

FOREIGN PATENT DOCUMENTS 0016988 10/1980 European Pat. Off. .

*Primary Examiner*—Lewis T. Jacobs
*Attorney, Agent, or Firm*—Sprung Horn Kramer & Woods

[57] ABSTRACT

In a polysiloxane-based composition which crosslink by addition, comprising (a) an organosiloxane with two or more vinyl groups in the molecule, (b) and organohydridopolysiloxane, as a crosslinking agent, (c) a catalyst for accelerating the addition reaction, (d) a hydrophobic filler and (e) optionally a dyestuff pigment, the improvement which comprises (f) hydrogenated castor oil as a structuring agent. The composition is highly viscous and will not run but can readily be stirred.

7 Claims, No Drawings

SILICONE PASTES FORMULATED WITH A STRUCTURAL VISCOSITY FOR IMPRESSION MATERIALS

The present invention relates to silicone pastes which are formulated with a structural viscosity by means of hydrogenated castor oil and are suitable for producing exact impressions of teeth and mucous membranes. The pastes according to the invention are cold-vulcanizing two-component silicone rubber systems of a "base paste" and a "catalyst paste", which are mixed with one another immediately before use and then crosslinked after about 2 to 5 minutes at room temperature.

Silicone pastes are widely used for making impressions of teeth. In general, they consist of a silicone oil which is mixed with fillers and is based on a polydimethylsiloxane with terminal hydroxyl groups, and is obtainable in various consistencies, depending on the method of application, and a liquid or paste-like hardener component containing a metal salt of a monocarboxylic acid, as the catalyst, and a silicic acid ester, as the crosslinking agent. Before use, the two components are mixed and then crosslinked, having been applied to impression spoons, in the mouth of the patient within about 2 to 5 minutes as a result of a polycondensation reaction, to give a polymer with a rubbery consistency.

Impression materials which are based on vinyl silicones and crosslinked by a polyaddition reaction have been known for some years. These materials consist of two pastes, a base paste containing silicone oil, filler and crosslinking agent and a catalyst paste consisting of silicone oil, fillers and catalyst.

The silicone oil is a polydimethylsiloxane containing terminal vinyl groups, the crosslinking agent contains polydimethylsiloxanes with reactive SiH groups and the catalyst consists of a platinum complex. Apart from a higher dimensional accuracy of the impression, systems which crosslink by addition also have the advantages of easier metering of the base and catalyst paste, due to the same paste viscosity and the matched mixing ratios of 1:1 of the two pastes, and that the pastes have no taste or odor.

In dentistry, impressions are produced by various methods, such as, for example, the double-mixing, double-impression and one-phase technique, which have as a precondition pastes in various classes of viscosity, such as, for example, kneadable or of high, medium or low viscosity. The viscosity of the silicone oil, the ratio of silicone oil to filler, the affinity of the filler for the silicone oil ("oil number"), the density and the specific surface area of the filler influence the viscosity of the paste.

Calcium silicate, calcium carbonate, calcium sulphate, talc, pumice flours, quartz flours and cristobalite flours are as a rule used as fillers in impression materials which crosslink by condensation and are based on polydimethylsiloxanes containing terminal hydroxyl groups. In order to prevent sedimentation of the fillers in the pastes, highly disperse silicic acids and emulsifiers such as ethoxylated fatty alcohol (U.S. Pat. No. 3,082,527), castor oil or paraffin/vaseline (French Pat. No. A-2,366,334) are added.

The spectrum of fillers which can be used in impression materials which crosslink by addition and are based on polydimethylsiloxanes containing terminal vinyl groups is substantially smaller. Thus, fillers can introduce traces of sulphur, iron, nickel or tin into the paste and thus deactivate platinum catalysts. On the other hand, moisture and/or SiOH groups on the surface of the filler react with the SiH groups of the crosslinking agent to form hydrogen, especially if aqueous filler suspensions display a basicity or acidity. Calcium carbonate, quartz flours and cristobalite flours, the surfaces of which are preferably charged with substances based on silazane or other surface coatings based on silicone, are in general used as fillers in these pastes. The tendency towards sedimentation is reduced with highly disperse silicic acids, the surfaces of which should likewise be charged.

It has been possible to achieve structural viscosity properties and/or thixotropic properties in silicone impression materials by addition of highly disperse silicic acids. However, this effect has never been consciously used to obtain materials which crosslink by addition and which, after mixing of the base paste and catalyst paste, have a low viscosity when applied to the preliminary impression or when forced out of the syringe and exhibit an increase in viscosity in the mouth of the patient as a result of the structural viscosity, this increase in viscosity preventing the material from dripping from the teeth and/or from running into the pharyngeal cavity. The reason for this is that in the case of the highly disperse silicic acids, the production of the thixotropy and/or structural viscosity in the pastes, on the one hand, is effected by SiOH groups on the surface of the silicic acid, but, on the other hand, as described above, the SiOH groups should be blocked by treatment with silazanes before the highly disperse silicic acids are used in the vinylsilicone impression materials. Highly disperse silicic acids are thus excluded as structuring agents for such materials.

It has now been found that hydrogenated castor oil builds up an outstanding structural viscosity in silicone impression materials which crosslink by addition, without adversely influencing the storage stability of the base paste and catalyst paste of the vinylsilicone impression materials.

It is known from European Pat. No. A-0,016,988 that certain surface-active substances can be used as thixotropic auxiliaries for silicone materials which crosslink by condensation. This technical doctrine, however, cannot be applied to systems which crosslink by addition without reservation:

Thus, for example, the thixotropic auxiliaries preferred according to European Pat. No. A-0,016,988, that is to say glycerol mono-distearate polyglycol ethers, lead to an impairment in the catalyst activity in pastes which crosslink by addition and are thus unsuitable for practical use in such systems.

The invention relates to materials which crosslink by addition, are based on polysiloxane and contain (a) an organosiloxane with two or more vinyl groups in the molecule, (b) an organo-hydridopolysiloxane, as a crosslinking agent, (c) a catalyst for accelerating the addition reaction, (d) hydrophobic fillers and, if appropriate, (e) dyestuffs, which are characterized in that they additionally contain hydrogenated castor oil as a structuring agent.

The invention also relates to the use of pastes which have been rendered thixotropic according to the invention and have structural viscosity as impression materials, in particular for impressions of teeth and mucous membranes.

The pastes according to the invention preferably contain 0.1 to 3% by weight, particularly preferably 0.2 to 1.8% by weight, based on the total paste, of hydrogenated castor oil.

A main advantage of the vinyl silicone pastes according to the invention is their structural viscosity. When the pastes are squeezed out of the tube, stable strands are obtained, as a result of their high viscosity, and these allow accurate metering of the base paste and catalyst paste. On the other hand, mixing of the two pastes is facilitated by the decrease in viscosity as a result of shearing forces. When the mixing operation has ended, however, the material immediately has a higher viscosity again, so that, after application to the impression spoon, it cannot run off When the filled impression spoon is introduced into the mouth, the viscosity again becomes lower in the region of the parts of which an impression is to be taken (teeth, mucous membrane, jaw wall), and thus gives a good reproduction of the situation in the mouth; on the other hand, the material does not drip into the pharyngeal cavity of the patient, which can lead to a retching stimulation being triggered off and makes the impression useless. During application by means of a syringe, the mixture of base paste and catalyst paste is placed in a low-viscosity consistency (as a result of the shearing forces in the nozzle of the syringe), for example around the stumps of teeth of which an impression is to be made. As a result of a rapid build-up in viscosity, the material does not flow from the site of application and also does not drip into the pharyngeal cavity. On the other hand, the material runs together with the material on the impression spoon introduced immediately thereafter. An accurate impression of the situation in the mouth and (after an aqueous gypsum suspension has been passed in the impression and hardened) a true-to-detail reproduction of the gypsum model are the result of the vinyl silicone impression materials according to the invention.

Constituents of the vinyl silicone pastes according to the invention are silicone oil (a), crosslinking agent (b), catalyst (c), fillers (d), dyestuffs (e) and, finally, organic structuring agents (f).

The silicone oil (a) is a polydimethylsiloxane which is known per se and contains terminal vinyl groups, the viscosity of which can be in the range from 500 to 100,000 mPa.s at 20° C., depending on the desired consistency of the formulated paste.

The crosslinking agent (b) is a polydimethylsiloxane which is likewise known per se and contains hydrogen atoms on at least two silicon atoms in its molecule.

The catalyst (c) is, for example, a platinum complex which has been prepared from hexachloroplatinic-IV acid. These compounds are also known per se.

Fillers (d) are understood as meaning, for example, calcium carbonate, quartz flours and cristobalite flours, and precipitated and pyrogenically produced silicon dioxides, the surfaces of which have preferably been charged with substances based on silazane or other reactive functional silicone compounds.

Dyestuffs (e) are used to differentiate between the base and the catalyst paste and for checking the mixture. Inorganic and organic colored pigments are preferred.

The organic structuring agent to be used according to the invention is a hydrogenated castor oil, the melting range of which is preferably 80° to 95° C., in particular 82° to 90° C.

The following examples, in which all the parts denote parts by weight, illustrate the invention.

EXAMPLE 1 ( COMPARISON EXPERIMENT)

The base paste was prepared by mixing 340 parts of polydimethylsiloxane containing terminal vinyl groups and with a viscosity of 10,000 mPa.s at 20° C., 210 parts of polydimethylsiloxane containing terminal dimethylhydridosilyl groups and with a viscosity of 120 mPa.s. at 20° C., 430 parts of silanized extrafine quartz flour and 20 parts of inorganic colored p1gment in a kneader.

The catalyst paste was prepared by mixing 548 parts of polydimethylsiloxane containing terminal vinyl groups and with a viscosity of 5,000 mPa.s at 20° C., 450 parts of the abovementioned extrafine quartz flour, 1.8 parts of titanium dioxide and 0.2 part of a complex of platinum and divinyltetramethyldisiloxane in a kneader.

EXAMPLE 2 (COMPARISON EXPERIMENT)

The base paste was prepared by mixing 340 parts of polydimethylsiloxane containing terminal vinyl groups and with a viscosity of 10,000 mPa.s at 20° C., 210 parts of polydimethylsiloxane containing terminal dimethylhydridosilyl groups and with a viscosity of 120 mPa.s at 20° C., 380 parts of the extrafine quartz flour from Example 1, 50 parts of precipitated silicic acid, charged on the surface with silanes and with a specific surface area, measure d by the BET method, of 90 $m^2/g$, and 20 parts of inorganic oolored pigment in a kneader.

The catalyst paste was prepared by mixing 548 parts of polydimethylsiloxane containing terminal vinyl groups and with a viscosity of 5,000 mPa.s at 20° C., 400 parts of the extrafine quartz flour from Example 1, 50 parts of the abovementioned precipitated silicic acid, 1.8 parts of titanium dioxide and 0.2 part of the platinum siloxane complex according to Example 1 in a kneader.

EXAMPLE 3 (ACCORDING TO THE INVENTION)

The base paste was prepared by mixing 330 parts of polydimethylsiloxane containing terminal vinyl groups and with a viscosity of 10,000 mPa.s at 20° C., 200 parts of polydimethylsiloxane containing terminal dimethylhydridosilyl groups and with a viscosity of 120 mPa.s at 20° C., 450 parts of the extrafine quartz flour from Example 1, 18 parts of inorganic colored pigment and 2 parts of hydrogenated castor oil with a melting point of 85° C. in a kneader, the paste being warmed to 95° C. and then cooled, with stirring, to 25° C.

The catalyst paste was prepared by mixing 526 parts of polydimethylsiloxane containing terminal vinyl groups and with a viscosity of 5,000 mPa.s at 20° C., 470 parts of the extrafine quartz flour from Example 1, 1.8 parts of titanium dioxide, 2 parts of hydrogenated castor oil with a melting point of 85° C., the paste being warmed to 95° C. and then cooled, with stirring, to 25° C., and 0.2 part of the platinum-siloxane complex from Example 1 in a kneader.

EXAMPLE 4 (COMPARISON EXPERIMENT)

The base paste was prepared by mixing 245 parts of polydimethylsiloxane containing terminal vinyl groups and with a viscosity of 10,000 mPa.s at 20° C., 160 parts of polydimethylsiloxane containing terminal dimethylhydridosilyl groups and with a viscosity of 120 mPa.s at 20° C., 520 parts of the extrafine quartz flour from Example 1, 70 parts of the precipitated silicic acid from Example 2 and 5 parts of inorganic oolored pigment in a kneader.

The catalyst paste was prepared by mixing 408 parts of polydimethylsiloxane containing terminal vinyl groups and with a viscosity of 5,000 mPa.s at 20° C., 520 parts of the extrafine quartz flour from Example 1, 20 parts of the precipitated silicic acid from Example 2, 18 parts of titanium dioxide and 0.2 part of the platinum-siloxane complex from Example 1 in a kneader.

EXAMPLE 5 (ACCORDING TO THE INVENTION)

The base paste was prepared by mixing 250 parts of polydimethylsiloxane containing terminal vinyl groups and with a viscosity of 10,000 mPa.s at 20° C., 160 parts of polydimethylsiloxane containing terminal dimethylhydridosilyl groups and with a viscosity of 120 mPa.s at 20° C., 570 parts of the extrafine quartz flour from Example 1, 5 parts of inorganic oolored pigment and 15 parts of hydrogenated castor oil with a melting point of 85° C. in a kneader, the paste being warmed to 95° C. and then cooled, with stirring, to 25° C.

The catalyst paste was prepared by mixing 408 parts of polydimethylsiloxane containing terminal vinyl groups and with a viscosity of 5,000 mPa.s at 20° C., 575 parts of the extrafine quartz flour from Example 1, 18 parts of titanium dioxide, 15 parts of hydrogenated castor oil with a melting point of 85° C., the paste being warmed to 95° and then cooled, with stirring, to 25° C., and 0.2 part of the platinum-siloxane complex from Example 1 in a kneader.

After preparation, all the pastes were introduced into tubes with a capacity of 130 ml and an outlet opening of 6 mm in diameter, and were kept at 23° C. for 24 hours. A 10 cm long strand of paste was then squeezed out onto a mixing block. It was assessed whether the force required to squeeze the paste out of the tube is low or high and, on the other hand, whether the strand of paste is still stable or has already spread one minute after being squeezed out.

A rotation viscometer from Haake, and in particular the plate/cone device PK 100 with a 3° cone, measuring head M 500 and recorder RV 100 with the corresponding test protocols (Order Number 222-0068) was available for measuring the viscosity. The following data were entered on these test protocols:

| Temperature | 23° C. |
|---|---|
| Rotovisko | RV 100 |
| System | M 500 |
| Measuring device | I 3° |
| A | 83.5 |
| M | 8.73 |
| Program time $t_1$ | 0 |
| Program time $t_2$ | 1 |
| Program time $t_3$ | 0 |
| Shearing stress S $\tau$ | 10% $\tau$ (Examples 1–3) 20% $\tau$ (Examples 4 and 5) |
| Shear rate $S_D$ | 1% D |

The viscosity values shown below in Table 1 were calculated from the viscosity curves recorded, at point 0.2 and point 1.0 of the shear rate (x axis).

TABLE 1

| | 1 (Comparison) | | 2 (Comparison) | | 3 (according to the invention) | | 4 (Comparison) | | 3 (according to the invention) | |
|---|---|---|---|---|---|---|---|---|---|---|
| Paste | Base paste | Catalyst paste | Base paste | Catalyst paste | Base paste | Catalyst paste | Base paste | Catalyst paste | Base paste | Catalyst paste |
| Quartz + dyestuff | 45% | | 40% | | 47% | | 52.5% | | 57.5% | |
| Silicic acid | — | | 5% | | — | | 7% | | — | |
| Hydrogenated castor oil | — | | — | | 0.2% | | — | | 1.5% | |
| Force applied on squeezing out of the tube | slight | slight | slight | slight | slight | slight | increased | increased | slightly increased | slightly increased |
| Stability of the strand | none | none | moderate | moderate | good | good | moderate | moderate | very good | very good |
| Viscosity at | | | | | | | | | | |
| Point 0.2 | 12 Pa·s | 12 Pa·s | 39 Pa·s | 39 Pa·s | 60 Pa·s | 57 Pa·s | 195 Pa·s | 186 Pa·s | 391 Pa·s | 418 Pa·s |
| Point 1.0 | 12 Pa·s | 12 Pa·s | 26 Pa·s | 27 Pa·s | 26 Pa·s | 25 Pa·s | 100 Pa·s | 92 Pa·s | 127 Pa·s | 135 Pa·s |
| Point 0.2 | 12 Pa·s | 12 Pa·s | 30 Pa·s | 30 Pa·s | 57 Pa·s | 55 Pa·s | 114 Pa·s | 102 Pa·s | 364 Pa·s | 382 Pa·s |

It will be understood that the specification and examples are illustrative but not limitative of the present invention and that other embodiments within the spirit and scope of the invention will suggest themselves to those skilled in the art.

We claim:

1. In a polysiloxane-based composition which cross-link by addition, comprising (a) an organosiloxane with two or more vinyl groups in the molecule, (b) and organo-hydridopolysiloxane, as a crosslinking agent, (c) a catalyst for accelerating the addition reaction, (d) a hydrophobic filler and (e) optionally a dyestuff pigment, the improvement which comprises (f) hydrogenated castor oil as a structuring agent.

2. A composition according to claim 1, containing about 0.1 to 3% by weight of hydrogentated castor oil.

3. A composition according to claim 1, containing about 0.2 to 1.8% by weight of hydrogentated castor oil.

4. A composition according to claim 1, wherein the hydrogenated castor oil has a melting range from 80° to 95° C.

5. A composition according to claim 1, wherein the hydrogenated castor oil has a melting range from 82° to 90° C.

6. In the making of an impression wherein a composition is placed about a shaped mass and allowed to harden the improvement which comprises employing a composition according to claim 1.

7. In the making of a dental impression, the improvement which comprises employing a composition according to claim 1.

* * * * *